US012605243B2

(12) United States Patent
Gain et al.

(10) Patent No.: US 12,605,243 B2
(45) Date of Patent: Apr. 21, 2026

(54) METHOD FOR PRODUCING A PLURALITY OF IMPLANTS FROM A PREVIOUSLY REMOVED HUMAN OR ANIMAL CORNEA

(71) Applicants: UNIVERSITE JEAN MONNET SAINT ETIENNE, Saint Etienne (FR); MANUTECH-USD, Saint Etienne (FR); CENTRE NATIONAL DE LA RECHERCHE SCIENTIFIQUE, Paris (FR); CENTRE HOSPITALIER UNIVERSITAIRE, Saint Etienne (FR)

(72) Inventors: Philippe Gain, Lyons (FR); Gilles Thuret, St Bonnet les Oules (FR); Cyril Mauclair, Challain la Potherie (FR); Samy Albourgol, Saint Etienne (FR); Gregory Egaud, Jonzieux (FR)

(73) Assignees: UNIVERSITE JEAN MONNET SAINT ETIENNE, Saint Etienne (FR); MANUTECH-USD, Saint Etienne (FR); CENTRE NATIONAL DE LA RECHERCHE SCIENTIFIQUE, Paris (FR); CENTRE HOSPITALIER UNIVERSITAIRE, Saint Etienne (FR)

( * ) Notice: Subject to any disclaimer, the term of this patent is extended or adjusted under 35 U.S.C. 154(b) by 1125 days.

(21) Appl. No.: 17/629,253

(22) PCT Filed: Jul. 22, 2020

(86) PCT No.: PCT/EP2020/070690
§ 371 (c)(1),
(2) Date: Jan. 21, 2022

(87) PCT Pub. No.: WO2021/013892
PCT Pub. Date: Jan. 28, 2021

(65) Prior Publication Data
US 2022/0249222 A1 Aug. 11, 2022

(30) Foreign Application Priority Data

Jul. 22, 2019 (FR) ...................................... 1908274

(51) Int. Cl.
A61F 2/14 (2006.01)
A61F 9/008 (2006.01)
A61L 27/36 (2006.01)

(52) U.S. Cl.
CPC .......... *A61F 2/142* (2013.01); *A61F 9/00831* (2013.01); *A61F 9/00834* (2013.01);
(Continued)

(58) Field of Classification Search
CPC ...................................................... A61F 2/142
See application file for complete search history.

(56) References Cited

U.S. PATENT DOCUMENTS 5,909,380 A * 6/1999 Dubois ................... G06T 15/10
606/4
6,939,378 B2 * 9/2005 Fishman ................... A61F 2/14
623/4.1
(Continued)

FOREIGN PATENT DOCUMENTS

CN 113692265 B * 10/2024 ......... A61F 9/00804
EP 1007623 B1 10/2005
(Continued)

OTHER PUBLICATIONS

Examination Report issued by the Japanese Patent Office on Feb. 6, 2024 in connection with Japanese patent application No. 2022-504166, 4 pages.

(Continued)

*Primary Examiner* — Benjamin A Schiffman
(74) *Attorney, Agent, or Firm* — BCF LLP

(57) ABSTRACT
The invention concerns a cutting process for producing a plurality of implants from a previously removed human or
(Continued)

animal cornea, wherein the process comprises the following steps:

depositing (200) the cornea in a holding device, cutting (300), using a laser source, the cornea contained in the holding device to obtain a cut cornea, detaching (400) each implant from the cut cornea, decellularizing (500) each detached implant to obtain decellularized implants, lyophilizing (600) each decellularized implant to obtain lyophilized implants, sterilizing (700) each lyophilized implant to obtain sterilized implants, packaging (800) each sterilized implant to obtain packaged implants.

8 Claims, 5 Drawing Sheets

(52) U.S. Cl.
  CPC ....... *A61L 27/3604* (2013.01); *A61L 27/3683* (2013.01); *A61F 2009/00872* (2013.01); *A61F 2240/001* (2013.01); *A61L 2430/16* (2013.01)

(56) References Cited

U.S. PATENT DOCUMENTS

| | | | | |
|---|---|---|---|---|
| 9,901,601 | B2 * | 2/2018 | Kishida | A61K 35/30 |
| 10,092,393 | B2 * | 10/2018 | Muller | A61F 9/0081 |
| 10,188,097 | B2 * | 1/2019 | Gain | A01N 1/143 |
| 10,449,090 | B2 * | 10/2019 | Muller | A61F 9/00834 |
| 10,688,196 | B2 * | 6/2020 | Cavallo | A61K 9/06 |
| 11,083,565 | B2 * | 8/2021 | Barker | A61F 2/1451 |
| 11,229,201 | B2 * | 1/2022 | Gain | A01N 1/148 |
| 11,229,202 | B2 * | 1/2022 | Gain | A01N 1/148 |
| 11,234,864 | B2 * | 2/2022 | Romano | A61F 9/0084 |
| 11,351,062 | B2 * | 6/2022 | Bernard | A61F 9/009 |
| 11,974,569 | B2 * | 5/2024 | Gain | A61L 27/3691 |
| 12,329,632 | B2 * | 6/2025 | Klopotek | A61L 27/3641 |
| 12,350,144 | B2 * | 7/2025 | Klopotek | A61F 9/00836 |
| 2002/0183844 | A1 | 12/2002 | Fishman et al. | |
| 2008/0114386 | A1 * | 5/2008 | Iliakis | G16H 20/40 |
| | | | | 606/4 |
| 2009/0018532 | A1 * | 1/2009 | Salin | B23K 26/40 |
| | | | | 606/5 |
| 2011/0306954 | A1 * | 12/2011 | Morin | H01S 3/094003 |
| | | | | 606/4 |
| 2017/0027754 | A1 | 2/2017 | Muller | |
| 2017/0319329 | A1 | 11/2017 | Muller et al. | |
| 2018/0214306 | A1 * | 8/2018 | Chassagne | A61F 9/0084 |
| 2018/0289857 | A1 * | 10/2018 | Rafat | A61L 27/56 |

| | | | | |
|---|---|---|---|---|
| 2019/0038399 | A1 * | 2/2019 | Muller | A61F 9/00836 |
| 2020/0000965 | A1 * | 1/2020 | Klopotek | B65D 85/54 |
| 2022/0161370 | A1 * | 5/2022 | Muller | B23K 26/0624 |
| 2022/0241463 | A1 * | 8/2022 | Gain | A61L 27/3604 |
| 2022/0317129 | A1 * | 10/2022 | Chedotal | G01N 21/6458 |
| 2023/0181369 | A1 * | 6/2023 | Lopez | A61F 9/00831 |
| | | | | 606/4 |
| 2023/0218443 | A1 * | 7/2023 | Bischoff | A61F 2/142 |
| | | | | 606/4 |
| 2023/0293350 | A1 * | 9/2023 | Lopez | A61B 90/25 |
| | | | | 606/4 |

FOREIGN PATENT DOCUMENTS

| | | |
|---|---|---|
| FR | 3083978 A1 | 1/2020 |
| JP | 2016512492 A | 4/2016 |
| WO | 2013032009 A1 | 3/2013 |
| WO | 2014/140434 A1 | 9/2014 |
| WO | 2016174688 A1 | 11/2016 |
| WO | 2018047151 A1 | 3/2018 |
| WO | 2018/102329 A1 | 6/2018 |

OTHER PUBLICATIONS

Damgaard et al., "Biological Lenticule Implantation for Correction of Hyperopia: An Ex Vivo Study in Human Corneas", Journal of Refractive Surgery, vol. 34, No. 4, 2018, pp. 245-252.

Galal et al., "Human Anterior Lens Capsule as a Biologic Substrate for the Ex Vivo Expansion of Limbal Stem Cells in Ocular Surface Reconstruction", Cornea, vol. 26, No. 4, May 2007, pp. 473-478.

Hartmann et al., "Human and porcine anterior lens capsule as support for growing and grafting retinal pigment epithelium and iris pigment epithelium", Graefe's Arch Clin Ophthalmol (1999), 237: pp. 940-945.

Kopsachilis et al., "Descemet's membrane substrate from human donor lens anterior capsule", Clinical and Experimental Ophthalmology 2012; 40, pp. 187-194.

Nicolini et al., "The anterior lens capsule used as support material in RPE cell-transplantation", Acta Ophtalmol. Scand. 2000: 78: 527-531.

Spinozzi et al., "Evaluation of the Suitability of Biocompatible Carriers as Artificial Transplants Using Cultured Porcine Corneal Endothelial Cells", Current Eye Research, https://doi.org/10.1080/02713683.2018.1536215.

Van den Bogerd et al., "Characterizing human decellularized crystalline lens capsules as a scaffold for corneal endothelial tissue engineering", Journal of Tissue Engineering and Regenerative Medecine, Dec. 2017; 1-9.

Yoeruek et al., "Human Anterior Lens Capsule as Carrier Matrix for Cultivated Human Corneal Endothelial Cells", Cornea, vol. 28, No. 4, May 2009, pp. 416-420.

English abstract provided for FR3083978A1.

* cited by examiner

6

61

62

63

64

65

66

67

68

METHOD FOR PRODUCING A PLURALITY OF IMPLANTS FROM A PREVIOUSLY REMOVED HUMAN OR ANIMAL CORNEA

CROSS-REFERENCE TO RELATED APPLICATIONS

This application is a national phase filing under 35 U.S.C. § 371 of International Application No. PCT/EP2020/070690 filed on Jul. 22, 2020, which claims benefit of priority from French Patent Application No. 1908274 filed Jul. 22, 2019, the contents of which are hereby incorporated by reference in their entirety.

FIELD OF THE INVENTION

The present invention relates to the general technical field of producing implants from a human or animal cornea.

To be more precise, the invention relates to a process including the cutting of a cornea to produce a plurality of implants for ophthalmologic applications in humans or animals.

BACKGROUND OF THE INVENTION

The cornea is an essential component of a patient's eyesight: indeed, it is the window through which images from the outside world enter the eye.

There are a variety of ways in which a patient's cornea can be damaged—resulting in partial or total loss of eyesight or threat to the integrity of the eyeball—related to the patient's various conditions, such as corneal ulceration from infectious or immune causes that can lead to perforation, keratoconus that deforms the cornea, opacity in particular following an infection, deep corneal neovessels, or corneal edema due to corneal endothelial deficiency.

When the cornea is ulcerated and close to perforation, when it has become opaque, deformed or is perforated, the patient is likely to benefit from a graft. Such a graft may be total or partial, and of different shapes.

Furthermore, it is also possible to modify the dioptric power of the cornea, by inserting a implant in the form of a lenticule of a chosen shape, to correct presbyopia or ametropia (myopia or hyperopia), for example, by inserting this corneal lenticule either in a pocket produced within the corneal stroma or on the corneal surface under the surface epithelium. It is also possible to graft, to the posterior face of the cornea, a very thin corneal lamella covered with endothelial cells cultured in the laboratory to compensate for a deficiency in endothelial cells (tissue engineered endothelial keratoplasty, or TEEK).

Partial corneal transplantation consists of grafting a healthy corneal fragment from a donor to replace or to strengthen or to modify a portion of the recipient's diseased cornea. Such a corneal fragment can fill in missing tissue (deep ulceration, perforation), strengthen the cornea (keratoconus), modify the corneal curvature (presbyopia, ametropia), or act as a support to carry endothelial cells (endothelial graft).

However, due to a very low level of organ donation and a growing need for corneas, there is a worldwide shortage of corneas. This is why it would be highly advantageous to be able to optimize the number of implants performed from a single donor cornea.

Various cutting processes and devices have already been proposed to produce several implants in the form of lenticules.

Document US 2017/319329 describes, in particular, a system for forming corneal lenticules, the system including a first cutting apparatus and a second cutting apparatus. The first cutting apparatus including a laser (acronym for «Light Amplification by Stimulated Emission of Radiation») is configured to cut a donor cornea and form a corneal portion. To be more precise, the first cutting apparatus is configured to cut the donor cornea along an axis extending between an anterior surface and a posterior surface of the cornea. The second cutting apparatus is configured to form a plurality of lenticules from the corneal portion by forming a series of cross-sections in the corneal portion. The cornea between two consecutive cutting planes forms a lenticule. Each lenticule is then used to form a respective corneal implant.

A disadvantage of this type of device is that it does not allow precise cutting planes to be made. Indeed, the corneal portion may undergo antero-posterior displacements, in particular during the laser/cornea interaction, which is detrimental to the precision of the laser beam focusing.

Another disadvantage of this type of device is that the quality of the cutting planes decreases with depth. Indeed, the deeper the focal plane in the cornea, the greater the loss of laser beam efficiency. Furthermore, only a limited number of lenticules can be produced with this type of device.

Document US 2019/0038399 describes a process and system for cutting a cornea to produce a plurality of implants having a surface profile designed to generally match a shape of an implant site. The cutting process comprises:

i) positioning the cornea in a locking system including suction nozzles to lock the cornea by suction, ii) cutting a cornea to obtain a lamella, for example using a femtosecond laser source or a microkeratome, iii) cutting the lamella to obtain a plurality of lenticules, for example using a femtosecond laser source or a microkeratome, iv) shaping the lenticules using an excimer laser source to obtain a plurality of implants, v) repeating the preceding steps to obtain a plurality of implants from a new lamella.

A disadvantage of the solution described in US 2019/0038399 is that it requires several cutting and shaping steps to obtain an implant. Indeed, locking the cornea by suction may cause limited modifications of the corneal portions facing the suction nozzles, thus altering the final cutting quality, once the suction is released and the cornea has regained its shape.

Another disadvantage of the solution proposed in US 2019/0038399 is that it takes a lot of time to process a cornea. Indeed, the process according to US 2019/0038399 requires a cutting step (using a femtosecond laser source) and a shaping step (using an excimer laser source) for each lenticule to obtain a usable implant. Furthermore, steps i) to iv) must be performed for each new lamella cut.

Yet another disadvantage of the solution proposed in US 2019/0038399 is that the shelf life of the resulting implants is time-limited, and they may be difficult to store.

One aim of the present invention is to provide a process for cutting a previously removed cornea which overcomes at least one of the aforementioned disadvantages.

To be more precise, an aim of the present invention is to provide a process for optimizing the cutting of a cornea to produce a plurality of implants, for example by minimizing cutting waste and/or maximizing the quality of the cut implants.

BRIEF DESCRIPTION OF THE INVENTION

To this end, the invention provides a process for producing a plurality of implants from a previously removed human or animal cornea, remarkable in that the process comprises the following steps:

depositing the cornea in a holding device including first and second plates transparent to the laser beam emitted by a laser source, the cornea being positioned between the first and second plates to apply mechanical stress to the anterior and posterior faces of the cornea, cutting, using the laser beam, the cornea contained in the holding device to obtain a cut cornea, the cutting step comprising generating gas bubbles to form contours of the plurality of implants, detaching each implant from the cut cornea, decellularizing each detached implant to obtain decellularized implants, lyophilizing each decellularized implant to obtain lyophilized implants, sterilizing each lyophilized implant to obtain sterilized implants, packaging each sterilized implant to obtain packaged implants.

Preferred but non-limiting aspects of the cutting process according to the invention are as follows:

the implants may include:

at least one reinforcing implant including a circular blade with parallel faces, and/or at least one filling implant including:

a circular blade and a nipple protruding from one face of the circular blade, or a ring-shaped washer, and/or at least one (bi)convex implant, and/or at least one (bi)concave implant, and/or at least one implant serving as a cell culture support and including a circular lamella with parallel faces and a thickness less than that of the reinforcing implant;

the step consisting in depositing the cornea in a holding device may comprise the substeps consisting in:

positioning the holding device in the optical path of the laser beam generated by the laser source and orienting the holding device so that the first plate is closer to the laser source than the second plate, emitting the laser beam generated by the laser source through the first plate to form gas bubbles in the half-thickness of the cornea nearest the first plate, turning the holding device so that the second plate is closer to the laser source than the first plate, emitting the laser beam generated by the laser source through the second plate to form gas bubbles in the half-thickness of the cornea nearest the second plate;

the process may also comprise a step of determining cutting areas in the cornea, said cutting areas corresponding to surfaces of the cornea at which gas bubbles are to be formed during the cutting step;

the determination step may comprise the following substeps:

acquisition of an image of the cornea, estimation of the thickness and diameter of the cornea, determination of setting parameters of the holding device to apply the mechanical stress to the cornea;

the determination step may comprise the following substeps:

determining the desired implant types and their associated sizes, calculating the positions and shapes of the cutting areas to be made according to the types and sizes of the desired implants, and generating a cutting plane to minimize corneal tissue loss;

the determination step may comprise the following substep:

displaying the cutting plane, said cutting plane illustrating the cornea and the cutting areas;

the decellularization step may comprise the following substeps:

immersing the received cornea in a decellularization fluid, and rinsing the cornea with a rinsing liquid such as saline solution;

the step of depositing the cornea may comprise a substep consisting in applying a protein binding material—such as glutaraldehyde—to the cornea.

The invention also relates to a surgical kit for treating ocular pathology, remarkable in that the kit comprises at least one implant obtained by the process described above.

BRIEF DESCRIPTION OF THE DRAWINGS

Other features and advantages of the process according to the invention will be more readily apparent from the following description of several alternative embodiments, given by way of non-limiting examples, from the appended drawings wherein.

DETAILED DESCRIPTION OF THE INVENTION

Various examples of the process for cutting a cornea for the preparation of implants will now be described with reference to the figures. In these various figures, the equivalent elements are designated by the same numerical reference.

1. General Points

Figure 1:
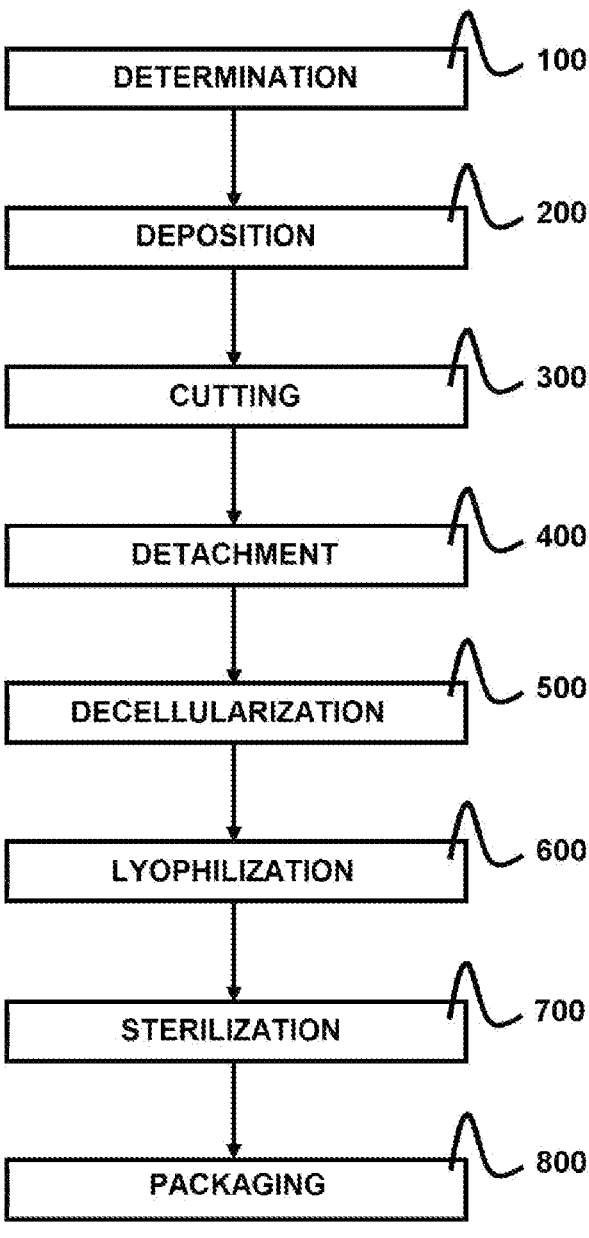
FIG. 1 is a schematic representation of the steps of a cutting process.

With reference to FIG. 1, the process for cutting a cornea 6 comprises the following steps:

Determining 100 the positions and shapes of the cutting areas in the cornea,

Depositing 200 the previously removed cornea in a cornea holding device,

Cutting 300, using a laser source, the cornea contained in the holding device to obtain a cut cornea, Detaching 400 each implant from the cut cornea, Totally decellularizing (keratocytes, dendritic cells and other immune cells) 500 each previously detached implant to obtain decellularized implants,

Lyophilizing 600 each decellularized implant to obtain lyophilized implants, Sterilizing 700 each lyophilized implant to obtain sterilized implants, Packaging 800 in a protective device allowing its rehydration in the operating room, and storing each sterilized implant to obtain packaged implants.

2. Detailed Description of the Steps of the Process for Preparing an Allograft or Xenograft Material

2.1. Determination

The determination step 100 is used to define the position and shape of the various cutting areas at which the cornea is to be cut during the cutting step 300. To be more precise, the determination step 100 is used to optimize the number of "pieces" produced within the same cornea (knowing that the thickness of a cornea may vary between 100 μm and 1800 μm, notably between 400 μm and 1500 μm, and in particular between 500 μm and 700 μm in the case of a human cornea), and that its diameter may vary from 10 to 13 mm in the case of a human cornea and from 10 to 20 mm in the case of an animal cornea.

The shape of each cutting area may vary depending on the type of implant the user wishes to make. In particular, each cutting area may be flat or curved (concave or convex) and extend along one (or more) substantially axial or transverse direction(s) in the cornea. The combination within the same cornea of cutting areas having different shapes (flat, curved, cylindrical, etc.) limits corneal tissue loss.

Figure 2:
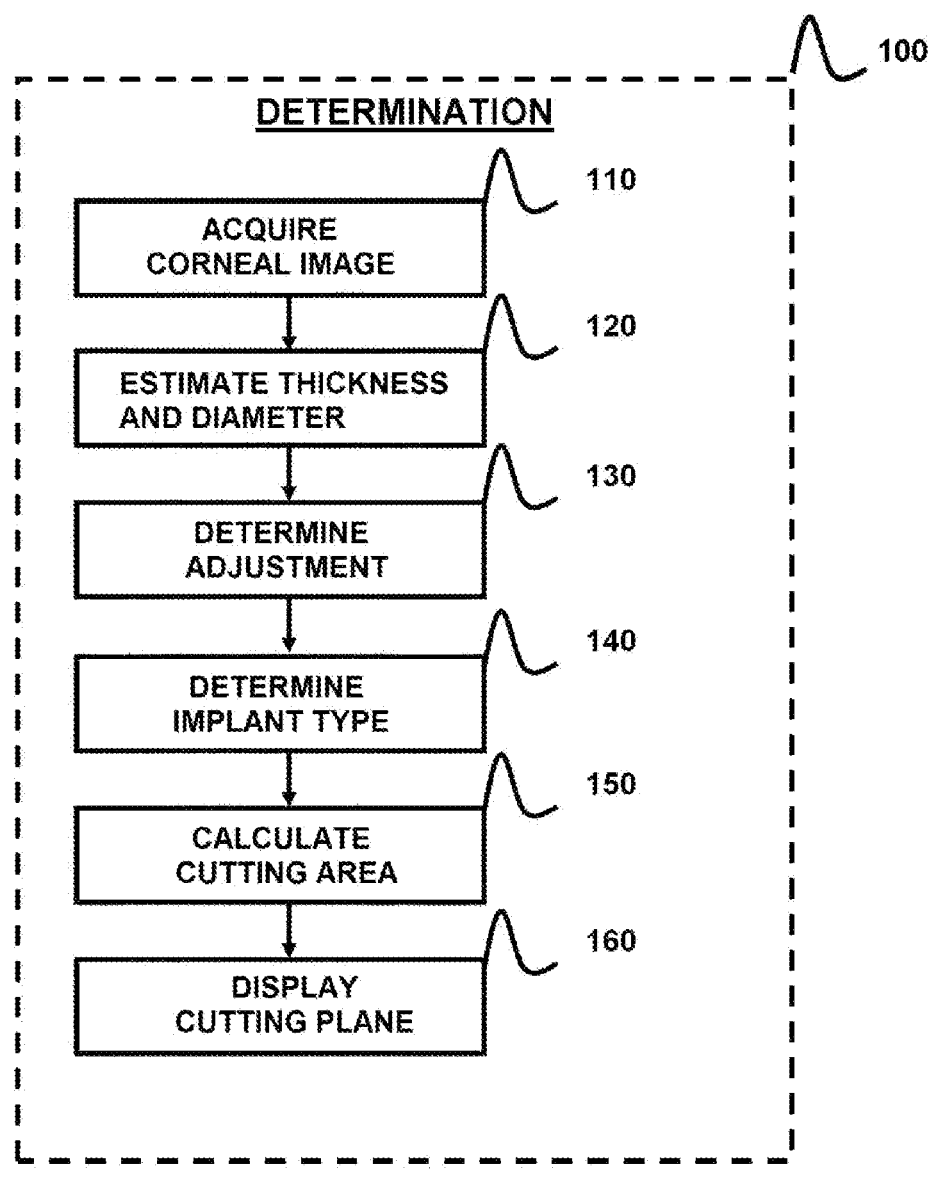
FIG. 2 is a schematic representation of the substeps of a phase for determining cutting planes in a cornea.

With reference to FIG. 2, the determination step 100 may comprise the following substeps:

i) Acquiring 110 an image of the cornea, ii) Estimating 120 the thickness and diameter of the cornea, iii) Determining 130 setting parameters of the holding device to apply mechanical stress to the cornea without crushing it, iv) Determining 140 the desired implant types (shapes) and their associated sizes, v) Calculating 150 the positions and shapes of the cutting areas to be made according to the types and sizes of the desired implants, and generating a cutting plane to minimize corneal tissue loss, vi) Displaying 160 (on display means such as a screen) the cutting plane illustrating the corneal tissue and the cutting areas to allow the user to visualize the cutting areas, vii) Sending the cutting plane to control means of a cutting device including the laser source.

The substep of acquiring 110 an image of the cornea to be cut may consist of the acquisition of an optical coherence tomography (OCT), Scheimpflug (visible light mapping), ultrasound biomicroscopy (UBM) or biomicroscopy (in front of or in a light slit) image or a simple photograph of the cornea. This image can be acquired using any image acquisition system known to the person skilled in the art.

From the acquired image(s), means for processing—including, for example, a processor and a memory—the acquired image(s) estimate 120 the thickness and the diameter of the cornea by implementing image processing techniques known to the skilled person. The processing means may also estimate the anterior and posterior curvatures of the cornea if the mechanical stress applied to the cornea is implemented using a holding device including curved plates.

The estimated thickness and diameter are then used by the processing means to determine 130 setting parameters of the holding device. In particular, in the case of a holding device as described in French patent application number FR1870835 dated 17 July 2018 (and which will be discussed in more detail hereinbelow), the processing means determines a distance between first and second plates of the holding device to apply a mechanical stress to the cornea without crushing it.

For example, the processing means implements the following formula:

$$D_{plates} = E_{tissue} - \text{Delta},$$

With:

$D_{plates}$: the distance between the first and second plates, $E_{tissue}$: the estimated thickness of the cornea, Delta: a fixed value (for example comprised between 50 and 500 μm).

These determined setting parameters are preferably displayed on display means (such as a screen) to allow the user to adjust the holding device in the subsequent depositing step 200.

The processing means then determines 140 the desired implant types and their associated sizes and shapes. In an embodiment of the invention, the desired implant types (and sizes) may be entered by the user using input means (such as a keyboard). Alternatively, the desired types (and sizes) of implants may be extracted from a database including predefined types of implants and their associated sizes. In this case, the processing means selects the implant types and sizes so as to minimize corneal tissue loss.

Figure 3:
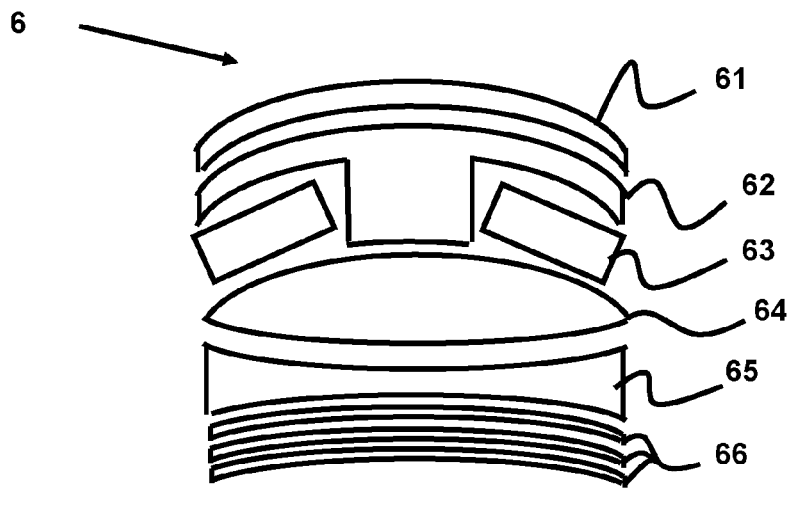
FIG. 3 is a schematic representation of multiple implants cut from a single cornea.

By way of indication, FIG. 3 illustrates various examples of implants 61-66 that may be cut from a cornea 6. Each implant may, for example, consist of:

a thick (for example greater than or equal to 100 μm) blade with parallel faces; such a blade can be used as a reinforcement plane for the treatment of keratoconus, a disease which induces a weakening of the biomechanics of the cornea, a "hat" implant 62 which can be used to plug a perforation that has occurred in a diseased cornea, such an implant having the general shape of a "hat" (ranging from a boater hat to a top hat) and including:

a circular (possibly curved) blade of large diameter, and a cylindrical (or truncated conical) nipple of smaller diameter protruding from one face of the circular blade, the circular blade having substantially the shape of an annular brim of a "hat", and the cylindrical nipple having substantially the shape of a more or less elevated cap ranging from a "boater hat" to a "top hat", a ring-shaped (optionally curved) or toroidal washer 63, such a washer being suitable for use in filling a circumferential ocular ulcer, a biconvex (or convex plane) lens 64, the diameter of which may, for example, be comprised between 2 (two) and 9 mm, such a lens being suitable for the treatment of presbyopia or hyperopia, a biconcave (or concave plane) lens 65, the diameter of which may, for example, be comprised between 5 and 9 mm, such a lens being suitable for the treatment of myopia, a lamella 66 with very thin (for example comprised between 40 and 50 μm) parallel faces suitable for constituting a support for the culture of endothelial cells in the context of a so-called endothelial graft.

Figure 4:
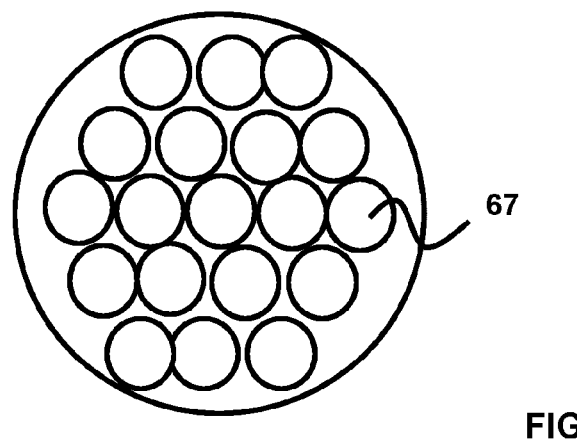
FIG. 4 is a schematic top-view representation of lenticules cut from a cornea.
Figure 5:
FIG. 5 is a schematic front-view representation of an alternative embodiment of a "hat" implant.

Of course, other types and shapes of implants can also be cut from a cornea 6 by implementing the process according to the invention. For example, with reference to FIG. 4, it is possible to cut a plurality of lenticules 67 of small diameter (about 2 millimeters). Furthermore, and as illustrated in FIG. 5, it is possible to cut one (or more) "hat" implant(s) with an eccentric nipple 68 (i.e., a "hat" implant in which the axes of revolution of the nipple and the circular blade are not coincident), for example for the treatment of a patient with an eccentric perforation of the eye.

Simultaneously or successively to the step of determining 140 the desired types of implants, the processing means calculate 150 the positions and shapes of the cutting areas. This calculation step may be implemented using any calculation technique known to the skilled person.

The calculation step 150 generates a cutting plane. This cutting plane may be displayed 160 to allow the user to view the cutting areas and possibly modify instruction parameters (adding a possible implant and/or increasing the dimensions of one (or more) implant(s) to minimize corneal tissue losses).

If the user modifies the instruction parameters, the preceding steps iv) to vi) are repeated. Otherwise, the cutting plane is transmitted to means for controlling the cutting device including the laser source.

2.2. Corneal Deposition

The deposition step 200 allows the cornea to be held in position for cutting by the laser source.

The deposition step 200 includes a substep of installing 220 the cornea in the holding device.

Figures 7, 8, 9:
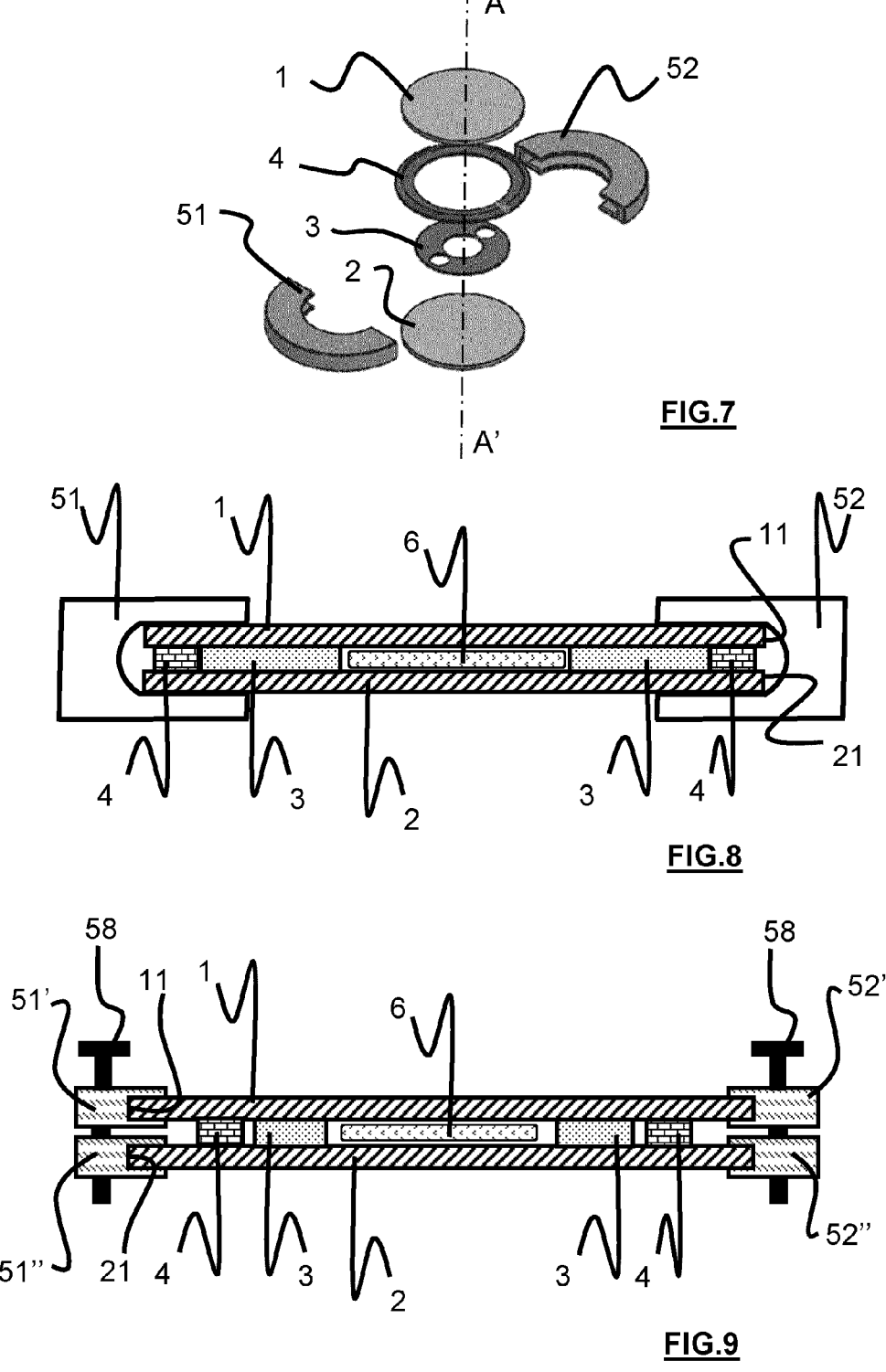
FIG. 7 is an exploded perspective view of the cornea holding device.
FIG. 8 is a cross-sectional view of the holding device once assembled.
FIG. 9 is a cross-sectional view of an alternative embodiment of the holding device once assembled.

Advantageously, the holding device may be of the type described in French patent application number FR1870835 dated 17 Jul. 2018. With reference to FIG. 7, such a holding device (which will be described in greater detail in section 3) comprises:

a stack of elements including:
  a first plate 1 transparent to electromagnetic radiation,
  a peripheral seal 4 positioned on the first plate 1, the peripheral seal 4 being intended to extend around the cornea,
  a second plate 2 transparent to electromagnetic radiation in contact with the peripheral seal 4,
  and a system for locking 51, 52 the stack of elements capable of pressing the first and second plates 1, 2 against the peripheral seal 4 so as to space the first and second plates 1, 2 by a distance comprised between 100 μm and 1800 μm, preferably between 400 μm and 1500 μm, and even more preferably between 500 μm and 700 μm.

Figure 6:
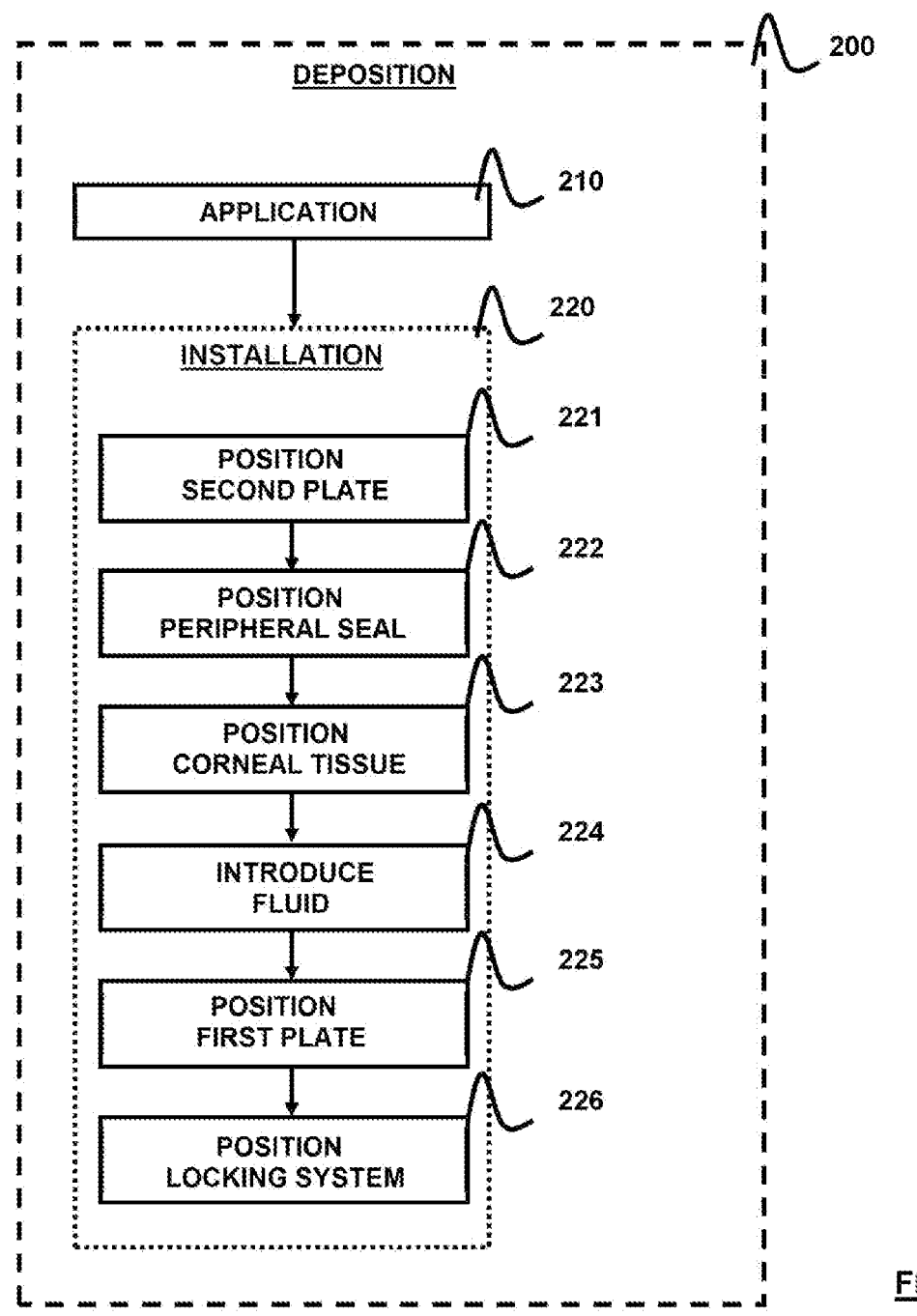
FIG. 6 is a schematic representation of the substeps of a phase of depositing the cornea in a holding device.

In this case and as illustrated in FIG. 6, the substep of installing 220 the cornea in the holding device described in FR1870835 comprises the following operations:
  positioning 221 the second plate 2 on a support,
  positioning 222 the peripheral seal 4 on the second plate 2 to define a housing for the cornea,
  positioning 223 the cornea in the housing,
  introducing 224 a fluid (liquid or gel) into the housing to perfect the transmission of the laser radiation generated by the laser source during the cutting step,
  positioning 225 the first plate 1 on the seal 4,
  fitting 226 the locking system 51-52 around the side edges of the first and second plates 1, 2.

The holding device is then assembled: the cornea is constrained between the first and second plates 1, 2. To be more precise, a mechanical stress is applied to anterior and posterior faces of the cornea by the first and second plates 1, 2 of the holding device according to FR1870835.

This mechanical stress limits the risks of displacement of the cornea during the subsequent cutting step 300.

This mechanical stress also allows finer and more precise cuts to be made by forcing the gas bubbles (produced by the laser beam during the cutting step) to escape from the cornea. The distance between adjacent cutting areas can thus be reduced, which allows a larger quantity of implants to be made from the same cornea.

Moreover, the application of a mechanical stress on the two faces of the cornea makes it possible to control its thickness. It is thus possible to make all the cuts of the cutting plane in a single run (i.e., prior to implementing the step of detaching 400 the implants) without multiple interventions, unlike the solution described in US 2019/0038399, which proposes cutting a lamella and then detaching it before cutting a following lamella (cutting then detaching then cutting then detaching, etc.), which multiplies the handling.

The step of depositing 200 on the holding device according to FR1870835 further allows the cutting step (of the cornea) to be performed under sterile and sealed conditions (closed vessel), unlike the solution according to US 2019/0038399 in which the suction locking system is open, which does not allow the successive cutting operations to be performed under sterile conditions.

In certain alternative embodiments, the deposition step 200 may comprise a substep consisting in applying 210 a protein binding-promoting solution—such as glutaraldehyde—to the cornea.

This application substep 210 allows for the fixing and crosslinking (i.e., the mechanical reinforcement by creating covalent bridges between the collagenous and/or proteoglycan proteins composing the stroma) of the cornea so that:
  it remains thin and transparent,
  it is easier to cut by applying the laser beam used during the cutting step,
  it is more rigid in order to facilitate the detachment step and the implants retain the shapes imposed by the cut areas, and
  it is permanently resistant to enzymatic degradation after implantation in the recipient.

This application substep 210 also has a sterilizing effect against certain bacteria and viruses.

The application 210 of the protein binding-promoting material may be implemented by any technique known to the skilled person (immersing the cornea in a protein binding-promoting fluid, projecting a protein binding-promoting fluid onto the cornea, etc.).

2.3. Cutting

The cutting step 300 generates a plurality of gas bubbles in the cut areas in order to facilitate subsequent detachment of the implants. The cutting step is implemented using a cutting system including a laser source.

To cut the cornea, an electromagnetic beam generated by the femtosecond laser source (delivering ultra-short, high-power pulses) can be used.

At each pulse, the femtosecond laser source generates a beam. This beam is focused (at a so-called "focusing" point) in the cornea 6. A gas bubble forms at the focusing point, generating a very localized disruption of the surrounding tissue.

To form a cutting plane in the cornea 6, a succession of small adjacent gas bubbles are generated by moving the beam. Thus, the gas bubbles are formed in the cutting area when cutting the cornea.

Advantageously, when using the holding device according to FR1870835, the cutting step consists in successively applying the electromagnetic beam generated by the laser source through both faces of the cornea (i.e., through the first and second plates of the holding device). Indeed, since the first and second plates of the holding device according to FR1870835 are transparent to electromagnetic radiation, it is possible to work on the cornea from both faces with the laser beam.

This makes it possible to limit the power of the laser beam required to form gas bubbles: since half of the cuts are made through one face and the other half through the opposite face, the laser beam only has to pass through half of the cornea at most. The energy used is thus lower, which limits the risks of damaging the cornea and increases the precision of the cut, during the implementation of the cutting step and consequently improves the quality of the implants.

2.4. Detachment

At the conclusion of the cutting step, a cut cornea is obtained in which the implants remain integral via the tissue microbridges extending between the plurality of gas bubbles generated.

The detachment step 400 consists in breaking these tissue bridges manually (or using an automated device) to detach the various implants from each other. This operation is performed by the user using surgical tools known to the skilled person.

2.5. Decellularization

The decellularization step 500 removes the keratocytes and/or endothelial cells and/or epithelial cells from each implant while maintaining its structure and conformation. This decellularization reduces the risk of an immune reaction in the transplanted patient.

The skilled person will appreciate that the decellularization step is carried out on each implant. This improves the quality of the decellularization, as it is more complete on portions of the cornea (here the implants may consist of thin lamellae, etc.) rather than on the entire cornea.

The decellularization step 500 thus produces decellularized implants with good biocompatibility and without deteriorating either the transparency or the biomechanical quality (resistance to handling during the manufacturing process or subsequently by the user surgeon). Its implementation can be based on different techniques using chemical means (use of fluids suitable for decellularization), and/or mechanical means (scraping, etc.).

For example, in an embodiment of the invention, the decellularization step 500 may comprise the following substeps:

immersing each implant in a decellularization fluid (including for example sodium chloride (NaCl), and/or ethylene diamine tetra acetic (EDTA), and/or a sodium dodecyl detergent and/or a DNase enzyme), and optionally subjecting each implant to mechanical vibration and/or mechanically scraping the surface of each implant, rinsing each implant with a rinsing fluid (such as saline solution), possibly repeating the preceding substeps if the implant still contains cells.

Implementation of the decellularization step 500 may be manual or automatic (for example, using a robot—such as a bath change robot that immerses each implant (for example, housed in a metal or plastic basket type wire mesh receptacle) in successive baths).

2.6. Lyophilization

The lyophilization step 600 dehydrates the implants. This lyophilization step facilitates the transportation and subsequent storage of the implants since they no longer need to be stored in a liquid medium.

The reader will appreciate that lyophilization reduces transparency and stiffens the implant, but in a completely reversible way after rehydration carried out in the operating room by the practitioner. Thus, the biomechanical qualities (resistance to surgical handling) are not altered once the implant is rehydrated.

The lyophilization step 600 may be implemented using a lyophilizer or using any other lyophilization technique known to the skilled person. Once the implant(s) is (are) lyophilized, it (they) is (are) subjected to a sterilization step.

2.7. Sterilization

The sterilization step 700 reduces the number of harmful organisms that may be attached in or to the lyophilized implant(s). The sterilization step 700 further increases the shelf life of the lyophilized implant(s).

The sterilization step 700 may be implemented by any sterilization technique known to the skilled person such as irradiation (for example, subjecting each lyophilized implant to electron beam radiation, gamma radiation, or ultraviolet light) for a period of time.

2.8. Packaging

At the end of the sterilization step 700, each implant is packaged 800 in packaging that allows sterile storage and transportation of the implant. The packaging also protects the implant from trauma and allows it to be rehydrated in the operating room.

By way of indication, the holding device according to FR1870835 will now be described in greater detail.

3. Holding Device

With reference to FIGS. 7 to 9, an example of a holding device used in the implementation of the cutting process according to the invention is shown.

The device comprises:

first and second plates 1, 2 transparent to electromagnetic radiation, possibly a spacer 3 to be positioned between the first and second plates 1, 2, a peripheral seal 4 to be positioned between the first and second plates, the peripheral seal extending around the spacer, a locking system 51-52 for the assembly of the plates 1, 2, the spacer 3 and the peripheral seal 4.

3.1. Transparent Plates

Each plate 1, 2 consists of one (or more) biocompatible, sterilizable material(s) transparent to electromagnetic radiation emitted by a radiation source—such as a laser or any other type of radiation source known to the skilled person for treating the cornea.

In the embodiment shown in FIG. 7, each plate 1, 2 is made of a single material, such as glass or poly(methyl methacrylate) or any other material known to the skilled person.

In certain alternative embodiments, each plate 1, 2 may be composed of a superposition of layers of different materials. For example, in an alternative embodiment, each plate 1, 2 is composed of a layer of rigid material (such as glass) extending between two layers of flexible material (for example silicone based):

the layer of rigid material increases the mechanical strength of the plate 1, 2, while the layers of flexible material limit the risk of dispersion of pieces of the rigid material layer in case of breakage thereof.

Each plate 1, 2 may also comprise reinforcements to increase its mechanical strength. The reinforcements extend, for example, at the edges 11, 21 of the plate 1, 2. The reinforcements may consist of rods of rigid material—such as titanium or stainless steel or any other biocompatible metal known to the skilled person—embedded in the plate 1, 2.

Alternatively, the reinforcements may be of the same material as the plate 1, 2. For example, the reinforcements may consist of one (or more) peripheral area(s) of the plate 1, 2 having a thickness (or thicknesses) greater than the thickness of a central area of the plate 1, 2. Thus, the plate 1, 2 may comprise thickened areas to enhance its mechanical strength and thinned areas for improved transmission of electromagnetic radiation.

Each plate 1, 2 may extend substantially in a plane or may be concave/convex, the curvature (or lack of curvature) of each plate 1, 2 depending on the intended application. In all cases, the first and second plates are intended to extend parallel to each other. In the context of the present invention, the expression "parallel flat/concave/convex plates" is understood to mean plates whose spacing is constant at any point. Thus, the distance between the first and second plates is constant, and comprised between 100 µm and 1800 µm, preferably between 400 µm and 1500 µm, and even more preferably between 500 µm and 700 µm. This mechanically constrains the anterior and posterior faces of the cornea 6 to ensure its locking in position in the holding device.

In the embodiment shown in FIG. 7, each plate 1, 2 is circular in shape. However, it is obvious to the skilled person that other shapes are possible for each plate 1, 2 (square, rectangular, triangular, etc.).

3.2. Spacer

The spacer 3 constitutes an intermediate part intended to be positioned between the first and second plates 1, 2. It maintains a predefined distance between the first and second plates 1, 2.

The spacer also limits the movement of the cornea in the plane perpendicular to a longitudinal axis A-A' of the device.

The spacer 3 is preferably rigid. However, the spacer 3 may also be elastically deformable. The spacer 3 is, for example, made of a biocompatible and sterilizable material, in particular a silicone-based material.

The spacer 3 comprises one (or more) main hole(s). The main hole may be circular or have any other desired shape (square, rectangular, etc.). The side wall of each main hole defines, together with the inner faces of the first and second plates 1, 2, a housing for containing a cornea 6.

Preferably, the diameter of the orifice is substantially equal to the diameter of the cornea 6 to laterally constrain the latter.

Advantageously, the spacer 3 may also comprise one (or more) degassing compartment(s). This (or these) degassing compartment(s) allow(s) storage of the gas bubbles formed in the cornea 6 during the application of electromagnetic radiation in view of its cutting.

Each compartment may be connected to one (or more) main hole(s) via a connecting channel (or channels). This (or these) channel(s) allow(s) routing of the gas bubbles formed in the cornea 6 to the degassing compartment.

3.3. Peripheral Seal

The peripheral seal 4 ensures the lateral sealing of the device once the transparent plates 1, 2 are assembled, in particular at the edges 11, 21 of the first and second plates 1, 2.

Advantageously, the peripheral seal 4 is made of a biocompatible and sterilizable elastomer material, for example silicone-based.

The peripheral seal 4 may be ring-shaped. However, it is obvious to the skilled person that the peripheral seal 4 may have other shapes (square, rectangular, triangular, etc.), in particular depending on the shape of the first and second plates 1, 2.

The thickness of the peripheral seal 4 and the thickness of the spacer 3 define the distance between the first and second plates 1, 2, and thus the mechanical thickness stress applied to the cornea 6 by said plates 1, 2. Seals 4 and spacers 3 of several thicknesses may be provided to adapt the thickness of the device to the thickness of the cornea 6, or to specific user choices. In particular, in an embodiment, the thickness of the peripheral seal (and/or of the spacer) may be comprised between 100 µm and 1800 µm, preferably between 400 µm and 1500 µm, and even more preferably between 500 µm and 700 µm. This spaces the first and second plates apart by a distance that ensures the mechanical stress of the anterior and posterior faces of the cornea 6 in order to ensure the locking in position of the cornea 6 in the holding device.

Alternatively, the seal 4 and the spacer 3 may be made of an expandable and/or compressible material that adapts to different distances between the first and second plates 1, 2. In this case, the adjustment of this distance is ensured by the locking system 51, 52 so that the first and second plates are spaced apart by a distance comprised between 100 µm and 1800 µm, preferably between 400 µm and 1500 µm, and even more preferably between 500 µm and 700 µm.

3.4. Locking System

The locking system 51, 52 holds in position the assembly composed of the first and second plates 1, 2, the seal 4 and the possible spacer 3. It guarantees the stability of this assembly and allows it to be handled by the user without any risk of unintentional opening.

The locking system 51,52 is removable to allow:

insertion of the cornea 6 into the device prior to its cutting, recovery of the implants once the cornea has been cut out.

With reference to FIG. 7, the locking system may comprise a frame intended to encircle the edges 11, 21 of the first and second plates 1, 2. The frame may be composed in two parts, in particular the frame may include first and second portions 51, 52.

Each portion 51, 52 consists, for example, of a half-cylinder including a central through-lumen extending along the longitudinal axis A-A' of the device. To be more precise, each portion comprises upper and lower annular trays and a side wall:

the inner face of the upper tray is intended to face the outer face of the first plate 1, the inner face of the lower tray is intended to face the outer face of the second plate 2, and the inner face of the side wall is intended to face the edges 11, 21 of the plates 1, 2 and the outer face of the seal 4.

The upper tray and/or the lower tray of each portion 51, 52 may comprise one (or more) hole(s) for the passage of a fastening element—such as a screw having a threaded rod—for applying a force along the longitudinal direction A-A' and tending to press the plates 1, 2 against the seal 4 and the spacer 3. This fastening element also makes it possible to adjust the desired distance between the first and second plates 1, 2 (and thus the mechanical stress applied to the cornea 6).

The first and second portions 51, 52 may also comprise fastening means (not shown) to allow said portions to be made integral.

Alternatively, and as shown in FIG. 9, the locking system may comprise first and second elementary frames:

the first frame comprises first and second elementary portions 51', 52' intended to encircle the edge 11 of the first plate 1, and the second elementary frame comprises first and second portions 51", 52" intended to encircle the edge 21 of the second plate 2.

In this case, the first and second elementary frames are made integral by means of a plurality of micrometric screws 58 for adjusting the spacing between the first and second elementary frames, and thus the spacing between the first and second plates 1, 2, so that the distance between the first and second plates is comprised between 100 μm and 1800 μm, preferably between 400 μm and 1500 μm, and even more preferably between 500 μm and 700 μm.

4. Conclusions

The above-described process for cutting a cornea optimizes the recycling of human/animal corneas by cutting several implants from the same cornea.

By virtue of this cutting process, it is possible to obtain different types of implants:

filling implants, for example "hat-shaped" to repair ocular perforations or "washer-shaped" to repair circumferential ulcers, thick parallel-faced blades to reinforce the structure of keratoconus. These thick blades can also be used to reinforce corneal ectasias secondary to refractive surgeries, or weaknesses of the sclera (post-operative retinal detachment, wound), or to cover externalized anti-glaucoma valve drains, etc.

(bi)convex lenticules to correct presbyopia or hyperopia, (bi)concave lenticules to correct myopia.

The implants obtained by the cutting process keep their characteristics of transparency and solidity, without cells triggering an immune reaction. They can be stored at room temperature, with an extended shelf life, and can be used immediately after simple rehydration.

The combination of the above-described cutting process with the holding device according to FR1870835 has many additional advantages:

the fact that the first and second plates of the holding device are transparent to electromagnetic radiation makes it possible to work on the cornea from both faces (the laser beam used during the cutting step can be applied via the anterior face and via the posterior face of the cornea), and therefore to reduce the power of the laser beam in order to limit the risks of damage to the implants during cutting;

the retention of the cornea allows:

the cornea to be kept immobile, even when the cornea is subjected to light radiation, a known and stable constrained position to be obtained (it is thus possible to turn the device over without losing the reference marks to continue a cut initiated on one face and completed on the other), the combination of the first and second plates with the peripheral seal allows the cornea to be prepared in sterile and sealed conditions (closed vessel) and facilitates the handling of the cornea without compromising its sterility.

Furthermore, the use of a device for retaining the cornea by both faces allows a plurality of implants to be cut in a single step, unlike the solution described in US 2019/0038399, which requires cutting a lamella from the cornea, dissecting the lamella, cutting lenticules from the lamella, shaping the lenticules to obtain implants, and repeating the preceding steps to obtain implants from a new lamella. It further allows the use of a single femtosecond laser source to perform this cutting step, unlike the solution described in US 2019/0038399, which requires:

the use of a femtosecond laser source (or a microkeratome-type cutting device) for cutting a lamella and cutting the lenticules in the lamella, and the use of an excimer laser source to shape each lenticule to obtain the implants.

In addition, the lyophilization step increases the shelf life of the implants and facilitates their storage on the shelf.

The reader will have understood that many modifications can be made to the invention described above without materially departing from the new teachings and advantages described herein.

For example, in the foregoing description, the determination step is presented as being implemented prior to the step of depositing the cornea in the holding device. It is obvious to the skilled person that this determination step can be implemented after the deposition step.

The invention claimed is:

1. A cutting process for producing a plurality of implants from a previously removed human or animal cornea, wherein the process comprises the following steps:

depositing the cornea in a holding device including first and second plates transparent to a laser beam emitted by a laser source, the cornea being positioned between the first and second plates to apply mechanical stress to anterior and posterior faces of the cornea, cutting, using the laser beam, the cornea contained in the holding device to obtain a cut cornea, the cutting step comprising generating gas bubbles to form contours of the plurality of implants, detaching each implant from the cut cornea, decellularizing each detached implant to obtain decellularized implants, lyophilizing each decellularized implant to obtain lyophilized implants, sterilizing each lyophilized implant to obtain sterilized implants, packaging each sterilized implant to obtain packaged implants.

2. The cutting process as claimed in claim 1, wherein said implants include:

at least one reinforcing implant including a circular blade with parallel faces, and/or at least one filling implant including:

a circular blade and a nipple protruding from one face of the circular blade, or)

a ring-shaped washer, and/or at least one (bi) convex implant, and/or at least one (bi) concave implant, and/or at least one implant serving as a cell culture support and including a circular lamella with parallel faces and a thickness less than that of the reinforcing implant.

3. The cutting process as claimed in claim 1, wherein the step of depositing the cornea in a holding device comprises the following substeps:

positioning the holding device in an optical path of the laser beam generated by the laser source and orienting the holding device so that the first plate is closer to the laser source than the second plate, emitting the laser beam generated by the laser source through the first plate to form gas bubbles in a half-thickness of the cornea nearest the first plate, turn the holding device so that the second plate is closer to the laser source than the first plate, emitting the laser beam generated by the laser source through the second plate to form gas bubbles in a half-thickness of the cornea nearest the second plate.

4. The cutting process as claimed in claim 1, which further comprises a step of determining cutting areas in the cornea, said cutting areas corresponding to surfaces of the cornea at which gas bubbles are to be formed during the cutting step, wherein the determination step comprises the following substeps:

determining desired implant types and sizes, calculating positions and shapes of the cutting areas to be made according to the desired implant types and sizes, and generating a cutting plane to minimize corneal tissue loss.

5. The cutting process as claimed in claim 4, wherein the determination step comprises the following substeps:

acquisition of an image of the cornea using an image acquisition system, estimation of a thickness and a diameter of the cornea using a processing system including a processor and a memory, determination, using the processing system, of setting parameters of the holding device to apply the mechanical stress to the cornea.

6. The cutting process as claimed in claim 4, wherein the determination step comprises the following substep:

displaying the cutting plane, said cutting plane illustrating the cornea and the cutting areas.

7. The cutting process as claimed in claim 1, wherein the decellularization step comprises the following substeps:

immersing each detached implant in a decellularization fluid, and rinsing each detached implant with a rinsing liquid.

8. The cutting process as claimed in claim 1, wherein the step of depositing the cornea comprises a substep of applying a protein binding-promoting material to the cornea.

\* \* \* \* \*